United States Patent [19]

Magin et al.

[11] Patent Number: 5,858,921

[45] Date of Patent: Jan. 12, 1999

[54] GLYPHOSATE HERBICIDAL AND PLANT GROWTH REGULANT COMPOSITIONS AND THEIR USE

[75] Inventors: Ralph W. Magin; Joe D. Sauer; Dru L. DeLaet, all of Baton Rouge; Deborah A. Quebedeaux, Thibodaux, all of La.

[73] Assignee: Albemarle Corporation, Richmond, Va.

[21] Appl. No.: 672,832

[22] Filed: Jun. 28, 1996

Related U.S. Application Data

[63] Continuation-in-part of Ser. No. 627,170, Apr. 3, 1996, Pat. No. 5,710,103.

[51] Int. Cl.$^6$ ............................. A01N 25/30; A01N 57/02
[52] U.S. Cl. ................................................. 504/206
[58] Field of Search ............................................. 504/206

[56] References Cited

U.S. PATENT DOCUMENTS

| | | | |
|---|---|---|---|
| 3,799,258 | 3/1974 | Franz | 504/206 |
| 4,075,002 | 2/1978 | Drewe et al. | 71/92 |
| 4,400,196 | 8/1983 | Albrecht et al. | 71/86 |
| 4,475,942 | 10/1984 | Bakel | 71/86 |
| 4,481,026 | 11/1984 | Prisbylla | 71/86 |
| 4,844,734 | 7/1989 | Iwasaki et al. | 71/120 |
| 5,258,359 | 11/1993 | Kassebaum et al. | 504/206 |
| 5,317,003 | 5/1994 | Kassebaum et al. | 504/116 |
| 5,324,708 | 6/1994 | Moreno et al. | 504/206 |
| 5,464,806 | 11/1995 | Kassebaum et al. | 504/206 |
| 5,464,807 | 11/1995 | Claude et al. | 504/206 |

FOREIGN PATENT DOCUMENTS

| | | |
|---|---|---|
| 0274369 | 7/1988 | European Pat. Off. . |
| 0483095 | 4/1992 | European Pat. Off. . |
| 0498785 | 8/1992 | European Pat. Off. . |
| 0577914 | 1/1994 | European Pat. Off. . |
| 0617894 | 10/1994 | European Pat. Off. . |
| 8704595 | 8/1987 | WIPO . |
| 9516351 | 6/1995 | WIPO . |
| 9600010 | 1/1996 | WIPO . |

OTHER PUBLICATIONS

Wyrill, III, J.B. and Burnside, O. C.—"Glyphosate Toxicity to Common Milkweed and Hemp Dogbane as Influenced by Surfactants", *Weed Science,* vol. 25 Issue 3 (May), 1977, pp. 275–287.

*Primary Examiner*—S. Mark Clardy
*Attorney, Agent, or Firm*—Philip M. Pippenger

[57] ABSTRACT

Glyphosate formulations which are effective even when employed at dosages below the dosage currently recommended for post-emergent herbicidal or plant growth regulant use are described. They are formulated as water solutions or powders or granules of (a) one or more agriculturally acceptable salts of glyphosate, e.g., amine, ammonium, alkali metal, alkylsulfonium, alkylphosphonium, sulfonylamine, and/or aminoguanidine salts of glyphosate; (b) at least one water-soluble long chain aliphatic hydrocarbyl dimethyl amine oxide in which the hydrocarbyl group is a linear or substantially linear saturated or olefinically unsaturated aliphatic group having in the range of about 8 to about 22 carbon atoms; and (c) at least one water-soluble quaternary ammonium halide having in the range of about 8 to about 40 carbon atoms in the molecule.

50 Claims, No Drawings

GLYPHOSATE HERBICIDAL AND PLANT GROWTH REGULANT COMPOSITIONS AND THEIR USE

REFERENCE TO RELATED APPLICATION

This is a continuation-in-part of prior application Ser. No. 08/627,170 filed Apr. 3, 1996, now U.S. Pat. No. 5,710,103.

TECHNICAL FIELD

This invention relates to glyphosate formulations which are highly effective even when employed at dosages below the dosage currently recommended for post-emergent herbicidal use against undesired vegetation.

BACKGROUND

Glyphosate, N-(phosphonomethyl)glycine, is a well-known widely used herbicide. It is generally employed in the form of an agriculturally acceptable salt.

In U.S. Pat. No. 5,116,401 to D. C. Young it is pointed out that although glyphosate is a very active, broad spectrum, systemic, relatively environmentally safe herbicide, its solubility in water at 25° C. is only 1.2 weight percent and many of its homologs and salts are only slightly soluble or are essentially insoluble in water and organic solvents. Thus in practice, formulations of glyphosate salts with other components to enhance its solubility and its effectiveness are typically used.

Over the years a wide variety of substances, including surfactants, have been studied or proposed as adjuvants to enhance the effectiveness of glyphosate. For example, J. W. Kassebaum and H. C. Berk indicate in U.S. Pat. No. 5,317,003, that surfactants are usually employed to enhance the effectiveness of glyphosate when it is applied to the foliage of various plants, and that the most widely used surfactant in commercial compositions is an ethoxylated fatty amine. In addition, they refer to knowledge in the art that a particular surfactant used in an aqueous composition with a herbicide can enhance the effectiveness of the herbicide, whereas other surfactants have very little, if any, beneficial effect. They also note that some surfactants may exhibit antagonistic effects. As an example they cite the work of Wyrill and Burnside, *Weed Science, Volume* 25, (1977), pages 275–287 wherein, among other things, it was found that the surfactant ETHOQUAD 18/12 was relatively ineffective in enhancing phytotoxicity of glyphosate to hemp dogbane whereas in a separate experiment an analogous compound, ETHOQUAD 18/25, was one of the most effective surfactants tested.

Despite the extensive studies and efforts devoted to improving the performance of glyphosate, a need exists for a way of potentiating the effectiveness of glyphosate salts such as the amine, ammonium, sodium, alkylsulfonium, alkylphosphonium, sulfonylamine, and aminoguanidine salts thereof by means of an environmentally friendly aqueous formulation made from a small number of ingredients, wherein the amounts of each of the components, including the glyphosate, can be kept very small, and wherein the resulting composition provides clearly observable herbicidal action, especially against broadleaf vegetation, in a short period of time after application. It would be particularly desirable if this need could be fulfilled by use of readily available, cost-effective materials while at the same time avoiding the inclusion of polyvalent metal-containing and metalloid-containing components in the formulation.

This invention is deemed to fulfill the foregoing need in an effective and highly efficient manner.

THE INVENTION

This invention involves the discovery, inter alia, that certain combinations of tertiary amine oxides and quaternary ammonium compounds are highly effective as co-adjuvants for increasing the phytotoxic effectiveness of glyphosate against a number of common broadleaf plant species. Thus this invention makes it possible to achieve enhanced phytotoxic effectiveness in an aqueous solution formed from as few as three added ingredients, all of which are readily available in the marketplace. Moreover it is possible pursuant to this invention to employ the glyphosate herbicide in dosage levels substantially lower than currently recommended. Also, in many cases the co-adjuvants make it possible to bring about substantial reductions it) glyphosate dosage levels while each of them is used at still smaller dosage levels than required if only one of the adjuvants is used without the other. Moreover, the adjuvants used in the practice of this invention are in themselves environmentally friendly. Further, the formulation requires no polyvalent metal or metalloid components in its formation. Indeed the preferred compositions are devoid of metal and metalloid additive content, and most preferably contain only the elements C, H, O, N, P, and Cl or Br, and optionally S. Moreover, the liquid concentrates are most preferably formed using deionized water.

The co-adjuvants used in forming the formulations of this invention are one or more water-soluble long chain aliphatic hydrocarbyl dimethyl amine oxides in which the hydrocarbyl group is a linear or substantially linear saturated or olefinically unsaturated aliphatic group having in the range of about 8 to about 22 carbon atoms, and one or more water-soluble quaternary ammonium halides having in the range of about 8 to about 40 carbon atoms in the molecule. By water-soluble is meant that the component is soluble to at least the extent of 1% by weight in deionized water at 25° C. When used in forming an aqueous concentrate of this invention, the adjuvant should have a water solubility of at least 5% by weight in deionized water at 25° C.

In the practice of this invention, these co-adjuvants are typically employed in a weight ratio in the range of 1:5 to 5:1, respectively, and preferably in a weight ratio in the range of 1:3 to 3:1, respectively. From a cost-effectiveness standpoint, a weight ratio in the range of from 1:1.5 to 1.5:1, respectively, is especially desirable for providing rapid control of broadleaf and grassy weed species.

Pursuant to one of its embodiments this invention provides a method of controlling vegetation by applying to plant foliage, preferably by spraying, a solution (preferably a polyvalent metal-free and metalloid-free solution) containing an effective herbicidal or growth regulant amount of a composition formed by intimately mixing the following ingredients with water:

(a) at least one agriculturally acceptable salt of glyphosate, e.g., an amine, ammonium, alkali metal, alkylsulfonium, alkylphosphonium, sulfonylamine, and/or aminoguanidine salt of glyphosate;

(b) at least one water-soluble long chain aliphatic hydrocarbyl dimethyl amine oxide in which the hydrocarbyl group is a linear or substantially linear saturated or olefinically unsaturated aliphatic group having in the range of about 8 to about 22 carbon atoms; and (c) at least one water-soluble quaternary ammonium halide (preferably a chloride or bromide) having in the range of about 8 to about 40 carbon atoms in the molecule.

Another embodiment of this invention is a herbicide or growth regulant formulation which comprises a solution containing at least an effective herbicidal or plant growth regulant amount of a composition formed by intimately mixing components (a), (b) and (c) above with water. Optionally, one or more substances, most preferably that are not herbicides, or plant growth regulants, or surfactants, such as dyes, humectants, corrosion inhibitors, stickers, spreaders and thickeners, can be included as component (d) in these formulations.

Still another embodiment of this invention is a herbicide or plant growth regulant formulation which comprises a mixture in powder or granular form containing an effective herbicidal or plant growth regulant amount of a composition formed by intimately mixing together components (a), (b) and (c), and optionally including one or more of (d) above. Such compositions can also be formed by evaporating to dryness (e.g., by spray drying, extrusion or pan granulation) a solution of components (a), (b) and (c) above and optionally (d) above. Application of the powder formulations to vegetation as foliar dusts for effecting control of the vegetation constitutes another embodiment of this invention.

It will be appreciated that to effect control of undesired plant vegetation pursuant to this invention, recourse may be had to herbicidal activity whereby undesired vegetation is killed and/or to plant growth regulant activity whereby the further growth of the vegetation is stunted, inhibited and/or slowed without actually killing all of the undesired vegetation treated with the composition.

The herbicidal (phytotoxic) and the plant growth regulant compositions of this invention include aqueous concentrates which can be shipped and stored until diluted with more water on site to produce the final solution for application to the foliage as by spraying. Likewise the herbicidal and the plant growth regulant compositions of this invention include the more dilute aqueous solutions for use in application to the foliage. These more dilute aqueous solutions are preferably formed simply by suitably diluting a concentrate of this invention with water (if a powder or granular concentrate) or with more water (if a liquid concentrate) to achieve the appropriate herbicidal or plant growth regulant dosage, but alternatively, can be formed on site by intimately mixing the separate ingredients or sub-combinations thereof with sufficient water on site to achieve the appropriate dosage. Use of the solid or liquid concentrates of this invention is preferable as it is a much simpler operation and minimizes the possibility of blending errors. Moreover, if desired, other components such as fertilizers, penetrants, spreaders, stickers, etc., can be introduced into the final solution at the time the concentrate is blended with water to form the diluted solution for application to the foliage.

Component (a)

The identities and methods for the preparation of the glyphosate ingredient of the formulation are well known and are reported in the literature. See for example, U.S. Pat. No. 3,799,758 to J. E. Franz which describes amine salts and ammonium, alkali metal salts of glyphosate, and the production of glyphosate by such methods as the phosphonomethylation of glycine, the reaction of ethyl glycinate with formaldehyde and diethylphosphite, and the oxidation of the corresponding aminophosphinic compounds. Another method involves conducting a Mannich reaction with phosphorous acid and formaldehyde on iminodiacetic acid followed by controlled oxidation to N-(phosphonomethyl) glycine. Typically the amine of the glyphosate amine salts has a molecular weight of less than 300. A preferred amine salt of glyphosate is a salt formed with isopropyl amine. Of the alkali metal salts of glyphosate, sodium is the preferred cation. Inasmuch as glyphosate has more than one replaceable hydrogen atom, either or both of mono- and dialkali metal salts of glyphosate can be formed and used. The alkylsulfonium salts of glyphosate are described for example in U.S. Pat. No. 4,315,765 to G. B. Large, and analogous procedures can be used for producing alkylphosphonium salts. Of the alkylsulfonium and alkylphosphonium salts, the trimethylsulfonium salt of glyphosate is preferred. Sulfonylamine and aminoguanidine salts of glyphosate which are also suitable for use pursuant to this invention are disclosed in EP-A-0 088 180. The patent literature contains numerous additional references to various other methods for the production of glyphosate. See for example U.S. Pat. Nos. 4,851,159; 4,898,972; 4,937,376; 4,952,723; 5,061,820; and 5,072,033 to Fields Jr. et al.; 5,023,369 to Fields, Jr.; 4,853,159 to Riley et. al; and 5,047,579 to Glowka et al., as well as relevant references cited in these patents. Fields, Jr. et al. U.S. Pat. No. 4,965,403 describes a process for producing the alkali metal salts of glyphosate. Aqueous solutions of glyphosate salts devoid of other adjuvants are commercially available from Monsanto Company and these solutions are suitable for use in forming the compositions of this invention.

Component (b)

This component in the form added to the water or aqueous solution is one or more water-soluble long chain aliphatic hydrocarbyl dimethyl amine oxides in which the hydrocarbyl group is a linear or substantially linear saturated or olefinically unsaturated aliphatic group having in the range of about 8 to about 22 carbon atoms. Preferably the long chain group is an alkyl group, most preferably a straight chain primary or normal alkyl group. Of the alkyl dimethyl amine oxide adjuvants of this invention, those in which the alkyl group contains about 8 to about 16 carbon atoms are preferred, and those in which the alkyl group contains about 12 to about 14 carbon atoms are more preferred, especially where the alkyl group is linear. n-Dodecyl, dimethyl amine oxide is particularly preferred. Where the long chain group is olefinically unsaturated it will usually contain up to three olefinic double bonds and in the range of about 12 to about 22 carbon atoms. Of the water-soluble long chain unsaturated aliphatic hydrocarbyl dimethyl amine oxides, those having about 12 to about 18 carbon atoms in a substantially straight chain are preferred. As noted above, this component can be a single compound or a combination or mixture of two or more compounds. A few examples of such compounds include n-octyl dimethyl amine oxide, n-nonyl dimethyl amine oxide, n-decyl dimethyl amine oxide, n-undecyl dimethyl amine oxide, n-dodecyl dimethyl amine oxide, n-tridecyl dimethyl amine oxide, n-tetradecyl dimethyl amine oxide, n-pentadecyl dimethyl amine oxide, n-hexadecyl dimethyl amine oxide, n-heptadecyl dimethyl amine oxide, n-octadecyl dimethyl amine oxide, n-nonadecyl dimethyl amine oxide, n-eicosyl dimethyl amine oxide, n-heneicosyl dimethyl amine oxide, n-docosyl dimethyl amine oxide, 8-methyl-1-nonyl dimethyl amine oxide, 2,7-dimethyl-1-octyl dimethyl amine oxide, 1-dec-9-enyl dimethyl amine oxide, 6-methyl-1-undec-9-enyl dimethyl amine oxide, 1-dodec-8-enyl dimethyl amine oxide, 1-octadec-9-enyl dimethyl amine oxide, and the water-soluble isomers, analogs and homologs of the foregoing.

Component (c)

There are, in general, several types of water-soluble quaternary ammonium halides which can be utilized in the practice of this invention. In one type the compound has one saturated or olefinically unsaturated aliphatic hydrocarbyl group having in the range of about 6 to about 24 carbon atoms, and a total of up to about 36 carbon atoms in the molecule. This group is either saturated or olefinically unsaturated such as described above in connection with component (b), although of course in this case the group has about 6–24 carbon atoms and, in any given formulation, this group need not be the same as the long chain group in component (b). This first type of quaternary ammonium halides can be depicted by the formula:

$$R^1R^2R^3R^4N^\oplus X^\ominus$$

where $R^1$ is a saturated or olefinically unsaturated aliphatic hydrocarbyl group having in the range of about 6 to about 24 carbon atoms, each of $R^2$, $R^3$ and $R^4$ is an alkyl group having 1 to 4 and preferably 1 or 2 carbon atoms, and X is a halogen atom, preferably a bromine or chlorine atom. Preferably, the total number of carbon atoms in $R^1$, $R^2$, $R^3$ and $R^4$ is up to about 30 carbon atoms. Most preferably each of $R^2$, $R^3$, and $R^4$ is a methyl group. A few examples of these compounds are hexyl trimethyl ammonium chloride, hexyl triethyl ammonium chloride, hexyl tributyl ammonium chloride, heptyl trimethyl ammonium chloride, octyl trimethyl ammonium chloride, nonyl trimethyl amine chloride, decyl trimethyl ammonium chloride, undecyl trimethyl ammonium chloride, dodecyl trimethyl ammonium chloride, tridecyl trimethyl ammonium chloride, tetradecyl trimethyl ammonium chloride, hexadecyl trimethyl ammonium chloride, decyl ethyl dimethyl ammonium chloride, 7-methylnonyl trimethyl ammonium chloride, 3,4-dimethyloctyl trimethyl ammonium chloride, octadec-9-enyl trimethyl ammonium chloride, hexyl tripropyl ammonium bromide, octyl trimethyl ammonium bromide, nonyl trimethyl amine bromide, decyl trimethyl ammonium bromide, undecyl trimethyl ammonium bromide, dodecyl trimethyl ammonium bromide, tridecyl trimethyl ammonium bromide, tetradecyl trimethyl ammonium bromide, hexadecyl trimethyl ammonium bromide, decyl ethyl dimethyl ammonium bromide, 7-methylnonyl trimethyl ammonium bromide, 3,4-dimethyloctyl trimethyl ammonium bromide, octadec-9-enyl trimethyl ammonium bromide, and water-soluble isomers, analogs and homologs of the foregoing. Especially preferred are hexadecyl trimethyl ammonium bromide or chloride. Mixtures or combinations of two or more adjuvants of this first type can be used.

Another type of quaternary ammonium compounds used in making the formulations of this invention are water-soluble compounds having two same or different saturated or olefinically unsaturated aliphatic hydrocarbyl groups having in the range of about 6 to about 18 carbon atoms, and two methyl groups. Preferably, the total number of carbon atoms in the molecule is no more than about 30 carbon atoms. The respective aliphatic hydrocarbyl groups are either saturated or olefinically unsaturated such as described above in connection with component (b), although here, each group has about 6–18 carbon atoms and, in any given formulation, neither of these groups need be the same as the long chain group in component (b). This second type of quaternary ammonium halides can be depicted by the formula:

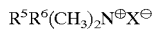

$$R^5R^6(CH_3)_2N^\oplus X^\ominus$$

where $R^5$ and $R^6$ are the same or different and each is a saturated or olefinically unsaturated aliphatic hydrocarbyl group having in the range of about 6 to about 18 carbon atoms, and X is a halogen atom, preferably a bromine or chlorine atom. Most preferably the total number of carbon atoms in the molecule is no more than about 24. A few examples of these compounds are bis(hexyl) dimethyl ammonium chloride, bis(heptyl) dimethyl ammonium chloride, bis(octyl) dimethyl ammonium chloride, bis (nonyl) dimethyl amine chloride, bis(decyl) dimethyl ammonium chloride, hexyl nonyl dimethyl ammonium chloride, decyl octyl dimethyl ammonium chloride, decyl dodecyl dimethyl ammonium chloride, bis(hexyl) dimethyl ammonium bromide, bis(6-methylheptyl) dimethyl ammonium bromide, bis(octyl) dimethyl ammonium bromide, bis(decyl) dimethyl ammonium bromide, decyl octyl dimethyl ammonium bromide, hexyl dodecyl dimethyl ammonium bromide, bis(hex-5-enyl) dimethyl ammonium bromide, bis(oct-4-enyl) dimethyl ammonium bromide, hept-6-enyl hexyl ammonium bromide, and water-soluble isomers, analogs and homologs of the foregoing. One or more water-soluble dialkyl dimethyl ammonium chlorides or bromides in which each of the two alkyl groups has in the range of from about 10 to about 16 carbon atoms are especially preferred. Mixtures or combinations of two or more of the compounds of this second type can be used.

A third type of quaternary ammonium halides useful in the practice of this invention is comprised of N-hydrocarbyl pyridinium halides. The hydrocarbyl group attached to the nitrogen atom of the heterocyclic aromatic ring of the pyridinium nucleus is a saturated or olefinically unsaturated aliphatic hydrocarbyl group having in the range of about 4 to about 18 carbon atoms. The pyridinium nucleus itself can be substituted with one or more short chain alkyl groups of up to about 4 carbon atoms each with the proviso that the total number of carbon atoms in the overall molecule is not more than about 24 carbon atoms. As in the prior types of component (c) compounds, the aliphatic hydrocarbyl group bonded to the nitrogen atom is either saturated or olefinically unsaturated such as described above in connection with component (b), although in any given formulation, this group need not be the same as the long chain group in component (b). Some examples of this type of quaternary ammonium halide are N-butyl pyridinium chloride, N-isobutyl pyridinium chloride, N-pentyl pyridinium chloride, N-hexyl pyridinium chloride, N-heptyl pyridinium chloride, N-octyl pyridinium chloride, N-isooctyl pyridinium chloride, N-decyl pyridinium chloride, N-dodecyl pyridinium chloride, N-tetradecyl pyridinium chloride, N-hexadecyl pyridinium chloride, N-octadecyl pyridinium chloride, N-pent-3-enyl pyridinium chloride, N-dec-9-enyl pyridinium chloride, N-dodec-6-enyl pyridinium chloride, N-oleyl pyridinium chloride, N-butyl pyridinium bromide, N-isobutyl pyridinium bromide, N-pentyl pyridinium bromide, N-octyl pyridinium bromide, N-decyl pyridinium bromide, N-dodecyl pyridinium bromide, N-2-ethylhexyl pyridinium bromide, and water-soluble isomer, analogs and homologs of the foregoing. N-dodecyl pyridinium bromide or chloride are especially preferred. Mixtures or combinations of two or more of the compounds of this third type can be used.

A fourth type of quaternary ammonium halides useful in the practice of this invention is comprised of compounds in which the four substituents on the nitrogen atom are one or two hydroxyalkyl groups, one long chain aliphatic hydrocarbyl group, and either one or two short chain alkyl groups, depending on whether there are one or two hydroxyalkyl groups in the molecule. This type of quaternary ammonium halides can be depicted by the formula:

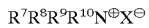

$$R^7R^8R^9R^{10}N^\oplus X^\ominus$$

where $R^7$ is a saturated or olefinically unsaturated aliphatic hydrocarbyl group having in the range of about 6 to about 24 and preferably in the range of about 10 to about 18 carbon atoms, $R^8$ is an alkyl group having 1 to 4 and preferably 1 or 2 carbon atoms, $R^9$ is a hydroxyalkyl group having from 2 to about 4 and preferably 2 carbon atoms, $R^{10}$ is, independently, either an alkyl group having 1 to 4 and preferably 1 or 2 carbon atoms or a hydroxyalkyl group having from 2 to about 4 and preferably 2 carbon atoms, and X is a halogen atom, preferably a bromine or chlorine atom. Preferably, the total number of carbon atoms in $R^7$, $R^8$, $R^9$ and $R^{10}$ is up to about 30 carbon atoms, and more preferably up to about 22 carbon atoms. Most preferably $R^7$ has in the range of about 10 to about 16 carbon atoms, $R^8$ is a methyl group, $R^9$ is a, hydroxyethyl group and $R^{10}$ is either a methyl group or a hydroxyethyl group. A few examples, of this fourth group of compounds are the $C_{10-18}$ (more preferably $C_{10-14}$) monoalkyl methyl diethanol quaternary ammonium chlorides and bromides (the bromides being more preferred), especially where the long chain alkyl group is a linear primary alkyl group, and the $C_{10-18}$ (more preferably $C_{10-14}$) monoalkyl dimethyl ethanol quaternary ammonium chlorides and bromides (the bromides being more preferred), especially where the long chain alkyl group is a linear primary alkyl group. n-Decyl methyl diethanol ammonium bromide, n-dodecyl methyl diethanol ammonium bromide, n-tridecyl methyl diethanol ammonium bromide, n-tetradecyl methyl diethanol ammonium bromide, n-decyl dimethyl ethanol ammonium bromide, n-dodecyl dimethyl ethanol ammonium bromide, n-tridecyl dimethyl ethanol ammonium bromide, and n-tetradecyl dimethyl ethanol ammonium bromide are illustrative examples.

In each of the above four types of quaternary ammonium halides, the halogen atom is preferably a chlorine or bromine atom. This invention contemplates use as component (c) of combinations or mixtures of (1) one or more quaternary ammonium compounds of the first above type with one or more quaternary ammonium compounds of the second above type; or (2) one or more quaternary ammonium compounds of the first above type with one or more quaternary ammonium compounds of the third above type; or (3) one or more quaternary ammonium compounds of the first above type with one or more quaternary ammonium compounds of the fourth above type; or (4) one or more quaternary ammonium compounds of the second above type with one or more quaternary ammonium compounds of the third above type; or (5) one or more quaternary ammonium compounds of the second above type with one or more quaternary ammonium compounds of the fourth above type; or (6) one or more quaternary ammonium compounds of the third above type with one or more quaternary ammonium compounds of the fourth above type; or (7) mixtures of one or more quaternary ammonium compounds of any three, or of all four, of the four above types of quaternary ammonium compounds.

Methods for producing the quaternary ammonium compounds used as component (c) in the practice of this invention are also well known and are reported in the literature. Typically they involve the quaternization of the appropriate tertiary amine by use of an appropriate lower alkyl halide such as methyl or ethyl bromide or chloride. Suitable compounds of the above formulas are available as articles of commerce.

Table 1 sets forth general and preferred proportions for use in forming the liquid concentrate formulations of this invention. The percentages given in Table 1 are weight percentages, and represent weight percent of the total composition. The percentages for the glyphosate salt such as amine, ammonium, alkali metal, alkylsulfonium, alkylphosphonium, sulfonylamine, and/or aminoguanidine or other agriculturally acceptable salt ("Glyphosate Salt") used in the practice of this invention as given in Table 1 are on an active ingredient basis and are in terms of glyphosate acid equivalent (i.e., the weight of the particular salt-forming portion of the product is excluded from the weight of the salt). Likewise the amount of any water associated with the salt as received is excluded from consideration as regards the percentages of the Glyphosate Salt shown in the table.

TABLE 1

| Ingredient | General Range, wt % | Preferred Range, wt % |
|---|---|---|
| (a) Glyphosate Salt | 0.1 to 65% | 18 to 65% |
| (b) Amine oxide | 1 to 35% | 10 to 20% |
| (c) Quaternary Salt | 1 to 35% | 10 to 20% |
| Other Ingredient(s) | 0 to 20% | 0 to 5% |
| Water | Balance to 100% | Balance to 100% |

Table 2 sets forth the proportions which can be used in forming the powder or granular compositions of this invention. As in Table 1, the percentages given in Table 2 are weight percentages on an active ingredient basis, and represent weight percent of the total composition. And as above, the percentages for the amine, ammonium, alkali metal, alkylsulfonium, alkylphosphonium, sulfonylamine, and/or aminoguanidine salt ("Glyphosate Salt") used in the practice of this invention as given in Table 2 are in terms of glyphosate acid equivalent.

TABLE 2

| Ingredient | General Range, wt % | Preferred Range, wt % |
|---|---|---|
| (a) Glyphosate Salt | 10 to 98% | 75 to 98% |
| (b) Amine oxide | 1 to 85% | 1 to 40% |
| (c) Quaternary Salt | 1 to 85% | 1 to 40% |
| Other Ingredient(s) | 0 to 20% | 0 to 5% |

The diluted solutions for application to the plant foliage are typically formed prior to application using a tank mixer, spray tank or similar apparatus. The dosage level of the composition applied to the plant foliage will depend to some extent upon the plant species being treated, and the prevailing weather conditions. Generally speaking, however, the amount applied will be a herbicidally effective amount falling within the range of about 50 to about 1250 grams of glyphosate (on an acid equivalent basis, i.e., excluding the weight of the cationic salt associated therewith) per hectare. In terms of ounces avoirdupois per acre this range corresponds (on the same acid equivalent basis) to about 0.7 to about 20 ounces of glyphosate per acre. In accordance with this invention it is preferred to employ a herbicidally effective amount (again on an acid equivalent basis) falling within the range of about 200 to about 830 grams of glyphosate per hectare which corresponds (on the same acid equivalent basis) to about 3 to about 12 ounces avoirdupois of glyphosate per acre, as this is generally sufficient to control most undesired plant species, is below the dosage currently recommended for herbicidal use of glyphosate formulations, and is thus more economical and environmentally friendly. On the basis of this disclosure and the new technology described herein, it is now possible to make departures from the foregoing ranges whenever such is deemed necessary or desirable in any given situation.

The following non-limiting Examples illustrate the practice and advantages of this invention.

EXAMPLES

A field test was conducted in which the effectiveness of various compositions of this invention was compared with effectiveness of a standard recommended glyphosate formulation. The test formulations of this invention consisted of the aqueous solution made from (a) N-(phosphonomethyl) glycine isopropyl amine salt, (b) dodecyl dimethyl amine oxide, (c) a quaternary ammonium halide, and water. No other component or ingredient was employed in forming these test formulations. Table 3 identifies the particular quaternary ammonium compounds used as component (c) in the formulations of the invention.

TABLE 3

| Formulation | Component (c) |
|---|---|
| A | bis(n-decyl) dimethyl ammonium chloride |
| B | n-hexadecyl trimethyl ammonium bromide |
| C | bis(n-decyl) dimethyl ammonium bromide |
| D | N-n-dodecyl pyridinium bromide |
| E | mixed dialkyl dimethyl ammonium bromide in which 40% of the alkyl groups were dodecyl, 50% were tetradecyl, and 10% were hexadecyl |

The glyphosate used in forming these formulations was ROUND-UP® D-Pak from Monsanto, which is a 62.0% aqueous solution of the glyphosate isopropyl amine salt in water with no other component therein. The control formulation was an aqueous solution of N-(phosphonomethyl)-glycine isopropyl amine salt and the commercial adjuvant INDUCE® (Helena Chemical Company) which, according to *A Guide to Agricultural Spray Adjuvants Used in the United States*, by T. L. Harvey, 1992–93 Edition, Thomson Publications, Fresno, Calif., page 33 is alkyl polyoxyalkane ether, free fatty acids and IPA, which is an adjuvant currently recommended for use in glyphosate formulations. The control formulation was applied at the recommended dosage level of 15 fluid ounces of glyphosate (active ingredient basis) per acre (624 grams of glyphosate per hectare) whereas the formulations of this invention were applied at dosages of only 5 and 10 fluid ounces of glyphosate (active ingredient basis) per acre (209 and 416 grams of glyphosate per hectare, respectively, on an active ingredient basis). All solutions contained one percent by weight of the particular adjuvant used, and the adjuvants of this invention were used in equal weights so that each test solution contained 0.5 wt % of component (b) and 0.5 wt % of component (c).

All tests were conducted at the same experimental test site at the same time, and were performed with three replicate tests for each composition, using randomized plots. Each plot was 10 feet by 15 feet (ca. 3.1 meters by ca. 4.6 meters) in size. Single applications were made between 10:00 a.m. and 2:30 p.m. on the same calm, sunny day with a relative humidity reading of 75% and an air/soil temperature of 85° F. and 92° F. (ca. 29° C. and ca. 33° C.), respectively. The application was made with a carbon dioxide pressurized back pack sprayer. The soil and leaf conditions were both dry at the time of application.

The population of weed species in the plots included the following:

1 to 3 square feet of morning glory (3–10 inches in height).

2 to 5 square feet of red weed (3–6 inches in height, with 3 to 6 leaves per plant).

3 to 5 square feet of sickle pod (3–7 inches in height, with 3 to 6 leaves per plant).

0 to 2 square feet of hemp sesbania (2–5 inches in height, with 3 to 5 leaves per plant).

1 to 4 square feet of barnyard grass and crab grass (3–5 inches in height, with 2 to 4 leaves per plant).

Observations of percentage of control were made at 7 days and 19 days after application, and Tables 4–8 summarize the results obtained in these tests. In Tables 4–8 the results are shown in terms of their statistical significance within 95% confidence limits. Thus the symbol ⊕ signifies that the test form of this invention gave results that statistically were equivalent to results given by the control. In every case the glyphosate dosage level in the formulations of this invention was only a fraction (33% or 67%) of the glyphosate dosage level in the control formulation. The symbol ⊙ signifies that statistically the result was only 1% below equivalence with the control, whereas the symbol ⊖ signifies that statistically the result was not equivalent to that of the control. The footnotes to Tables 4–8 give the results of the control tests at the full glyphosate dosage level.

TABLE 4

Control of Morning Glory Under Field Conditions

| Formulation | Glyphosate Dosage, % of Control | Result, 7 Days, % Control | Result, 19 Days, % Control |
|---|---|---|---|
| A | 33% | 55% ⊙ | 72% ⊕ |
| A | 67% | 73% ⊕ | 82% ⊕ |
| B | 33% | 53% ⊖ | 73% ⊕ |
| B | 67% | 83% ⊕ | 83% ⊕ |
| C | 33% | 62% ⊕ | 67% ⊕ |
| C | 67% | 78% ⊕ | 77% ⊕ |
| D | 33% | 65% ⊙ | 53% ⊖ |
| D | 67% | 75% ⊕ | 87% ⊕ |
| E | 33% | 67% ⊕ | 68% ⊕ |
| E | 67% | 67% ⊕ | 82% ⊕ |

Control: 73% after 7 days; 82% after 19 days.

TABLE 5

Control of Red Weed Under Field Conditions

| Formulation | Glyphosate Dosage, % of Control | Result, 7 Days, % Control | Result, 19 Days, % Control |
|---|---|---|---|
| A | 33% | 60% ⊙ | 70% ⊖ |
| A | 67% | 75% ⊕ | 83% ⊕ |
| B | 33% | 50% ⊖ | 70% ⊖ |
| B | 67% | 87% ⊕ | 87% ⊕ |
| C | 33% | 62% ⊕ | 68% ⊖ |
| C | 67% | 87% ⊕ | 93% ⊕ |
| D | 33% | 60% ⊙ | 73% ⊖ |
| D | 67% | 72% ⊕ | 83% ⊕ |
| E | 33% | 58% ⊖ | 73% ⊖ |
| E | 67% | 88% ⊕ | 87% ⊕ |

Control: 77% after 7 days; 93% after 19 days.

TABLE 6

Control of Sickle Pod Under Field Conditions

| Formulation | Glyphosate Dosage, % of Control | Result, 7 Days, % Control | Result, 19 Days, % Control |
|---|---|---|---|
| A | 33% | 50% ⊕ | 68% ⊕ |
| A | 67% | 58% ⊕ | 73% ⊕ |
| B | 33% | 38% ⊖ | 68% ⊕ |
| B | 67% | 53% ⊕ | 72% ⊕ |
| C | 33% | 38% ⊖ | 60% ⊕ |
| C | 67% | 63% ⊕ | 70% ⊕ |
| D | 33% | 32% ⊖ | 52% ⊖ |
| D | 67% | 51% ⊕ | 48% ⊖ |
| E | 33% | 45% ⊕ | 50% ⊖ |
| E | 67% | 57% ⊕ | 75% ⊕ |

Control: 62% after 7 days; 70% after 19 days.

TABLE 7

Control of Hemp Sesbania Under Field Conditions

| Formulation | Glyphosate Dosage, % of Control | Result, 7 Days, % Control | Result, 19 Days, % Control |
|---|---|---|---|
| A | 33% | 12% ⊙ | 75% ⊙ |
| A | 67% | 20% ⊕ | 83% ⊕ |
| B | 33% | 13% ⊖ | 70% ⊖ |
| B | 67% | 20% ⊕ | 87% ⊕ |
| C | 33% | 8% ⊖ | 70% ⊖ |
| C | 67% | 25% ⊕ | 93% ⊕ |
| D | 33% | 20% ⊕ | 72% ⊖ |
| D | 67% | 55% ⊕ | 83% ⊕ |
| E | 33% | 12% ⊙ | 77% ⊕ |
| E | 67% | 27% ⊕ | 87% ⊕ |

Control: 25% after 7 days; 90% after 19 days.

TABLE 8

Control of Barnyard Grass & Crab Grass Under Field Conditions

| Formulation | Glyphosate Dosage, % of Control | Result, 7 Days, % Control | Result, 19 Days, % Control |
|---|---|---|---|
| A | 33% | 47% ⊖ | 65% ⊖ |
| A | 67% | 80% ⊕ | 92% ⊕ |
| B | 33% | 58% ⊖ | 68% ⊖ |
| B | 67% | 92% ⊕ | 88% ⊕ |
| C | 33% | 40% ⊖ | 50% ⊖ |
| C | 67% | 92% ⊕ | 75% ⊙ |
| D | 33% | 50% ⊖ | 65% ⊖ |
| D | 67% | 90% ⊕ | 68% ⊖ |
| E | 33% | 80% ⊕ | 58% ⊖ |
| E | 67% | 90% ⊕ | 72% ⊖ |

Control: 93% after 7 days; 92% after 19 days.

Additional field tests were carried out in which the effectiveness of various additional compositions of this invention was compared with effectiveness of the above standard recommended glyphosate formulation. The test formulations of this invention consisted of the aqueous solution made from (a) N-(phosphonomethyl)glycine isopropyl amine salt, (b) n-octyl dimethyl amine oxide or n-tetradecyl amine oxide, (c) n-tetradecyl methyl diethanol ammonium bromide or n-tetradecyl dimethyl ethanol ammonium bromide, and water. No other component or ingredient was employed in forming these test formulations. Table 9 identifies the particular amine oxides and quaternary ammonium compounds used in the formulations of the invention in this group of tests.

TABLE 9

| Formulation | Component (b) | Component (c) |
|---|---|---|
| F | octyl dimethyl amine oxide | tetradecyl methyl diethanol ammonium bromide |
| G | octyl dimethyl amine oxide | tetradecyl dimethyl ethanol ammonium bromide |
| H | tetradecyl dimethyl amine oxide | tetradecyl methyl diethanol ammonium bromide |
| I | tetradecyl dimethyl amine oxide | tetradecyl dimethyl ethanol ammonium bromide |

As above, the glyphosate used in forming these formulations was ROUND-UP® D-Pak from Monsanto. The control formulation was an aqueous solution of N-(phosphonomethyl)glycine isopropyl amine salt and the currently recommended adjuvant INDUCE®, referred to above. The control formulation was applied at the recommended dosage level of 15 fluid ounces of glyphosate (active ingredient basis) per acre (624 grams of glyphosate per hectare) whereas the formulations of this invention were applied at dosages of only 10 fluid ounces of glyphosate (active ingredient basis) per acre (416 grams of glyphosate per hectare on an active ingredient basis). All solutions contained one percent by weight of the particular adjuvant used, and the adjuvants of this invention were used in equal weights so that each test solution contained 0.5 wt % of component (b) and 0.5 wt % of component (c).

All tests of this series were conducted at the same experimental test site at the same time, and were performed with four replicate tests for each composition, using randomized plots. Each plot was 8 feet by 15 feet (ca. 2.4 meters by ca. 4.6 meters) in size. Single applications were made between 9:30 a.m. and 11:30 a.m. on the same calm, sunny day with a relative humidity reading of 70% and an air/soil temperature of 89° F. and 88° F. (ca. 32° C. and ca. 31° C.), respectively. The application was made with a carbon dioxide pressurized back pack sprayer. The weed species populations were wild poinsettia (2–7 inches or 5.1–17.8 centimeters in height with 2–5 leaves per plant), and a combination of Johnson grass and barnyard grass (3–6 inches or 7.6–15.2 centimeters in height with 3–5 leaves per plant). The soil and leaf conditions were both dry at the time of application. Observations of percentage of control in the test plots were made 4 days, 7 days and 14 days after the application. No rainfall occurred in the first 24 hours after application. Thereafter the rainfall (in inches and in centimeters, respectively) was 0.11/0.28 in the first three days after application, 0.06/0.15 in days 4 to 7, and 0.95/2.4 during week two after application.

Observations of percentage of control in these tests are summarized in Tables 10 and 11. Tables 10 and 11 show the results in terms of their statistical significance within 95% confidence limits. Thus the symbol ⊕ signifies that the test formulation of this invention gave results that statistically were equivalent to results given by the control. The symbol ⊙ signifies that statistically the result was only 1% below equivalence with the control. The symbol ⊖ signifies that statistically the result was not equivalent to that of the control but nevertheless demonstrated growth regulant activity. In every case the glyphosate dosage level in the formulations of this invention was only a fraction (67%) of the glyphosate dosage level in the control formulation.

TABLE 10

Control of Wild Poinsettia Under Field Conditions

| Formulation | Result, 4 Days, % Control | Result, 7 Days, % Control | Result, 14 Days, % Control |
|---|---|---|---|
| F | 38% ⊕ | 49% ⊖ | 60% ⊙ |
| G | 48% ⊕ | 62% ⊕ | 75% ⊕ |
| H | 54% ⊕ | 66% ⊕ | 81% ⊕ |
| I | 60% ⊕ | 74% ⊕ | 90% ⊕ |

Control: 40% after 4 days; 44% after 7 days; 66% after 14 days.

TABLE 11

Control of Barn Yard Grass and Crab Grass Under Field Conditions

| Formulation | Result, 4 Days, % Control | Result, 7 Days, % Control | Result, 14 Days, % Control |
|---|---|---|---|
| F | 48% ⊕ | 66% ⊕ | 59% ⊕ |
| G | 51% ⊕ | 64% ⊕ | 78% ⊕ |

TABLE 11-continued

Control of Barn Yard Grass and Crab Grass Under Field Conditions

| Formulation | Result, 4 Days, % Control | Result, 7 Days, % Control | Result, 14 Days, % Control |
|---|---|---|---|
| H | 46% ⊕ | 62% ⊕ | 84% ⊕ |
| I | 51% ⊕ | 68% ⊕ | 81% ⊕ |

Control: 45% after 4 days; 46% after 7 days; 70% after 14 days.

Still additional field tests were conducted as described above in connection with the results summarized in Tables 10 and 11 with the following exceptions: Each randomized plot was 10 feet by 20 feet in size. The single applications were made between 9:30 a.m. and 11:30 a.m. on the same sunny day with a 2 to 3 mile per hour wind from the southwest and an air/soil temperature of 85° F. and 88° F. (ca. 30° C. and ca. 31° C.), respectively. The weed species was morning glory (3–7 inches or 7.7–17.8 centimeters in height with 3–6 leaves per plant). No rainfall occurred in the first 24 hours after application. Thereafter the rainfall (in inches and in centimeters, respectively) was 0.54/1.4 in the first three days after application, 1.32/3.3 in days 4 to 7, and 0.23/0.59 during week two after application. Two formulations of this invention were used. In formulations J and K, the amine oxide used was dodecyl dimethyl amine oxide. In formulation J, the quaternary ammonium salt used was dodecyl methyl diethanol ammonium bromide. The quaternary ammonium salt used in formulation K was dodecyl dimethyl ethanol ammonium bromide. Table 12 summarizes the results in the same manner as above.

TABLE 12

Control of Morning Glory Under Field Conditions

| Formulation | Result, 4 Days, % Control | Result, 7 Days, % Control | Result, 14 Days, % Control |
|---|---|---|---|
| J | 16% ⊕ | 69% ⊕ | 78% ⊕ |
| K | 15% ⊕ | 60% ⊕ | 72% ⊕ |

Control: 15% after 3 days; 56% after 7 days; 64% after 14 days.

Optionally, one or more other substances can be employed in the formulations of this invention provided no such substance materially detracts from the effectiveness of the composition in combatting the particular plant species to be controlled by use of the formulation. By "materially" in this context is meant that in tests conducted by concurrent application under identical conditions and using identical dosages of one or the other of two (2) test formulations to a plant species in three (3) identical pairs of test plots (each pair consisting of a Case I plot and a Case II plot) in the same substantially uniform test site, where in Case I the formulation of this invention does not contain such additional substance(s) whereas in Case II the identical formulation does additionally contain such additional substance(s), there is a reduction in the average percentages of the plant species controlled in the three (3) Case II plots as compared to the average percentages of the plant species controlled in the three (3) Case I plots, and the arithmetic difference between these averages exceeds 10%. Such other substances that may be used if they do not materially detract from the effectiveness of the composition include dyes, pigments, humectants, corrosion inhibitors, thickeners, adhering agents (stickers), spreading agents, other herbicides, and like materials. Such other substances can be introduced into the water in any sequence relative to components (a), (b) and (c) thereof, i.e., such materials can be added before, after or at the same time as any one or two, or all three of components (a), (b) and (c). In this connection, while one or more additional herbicides can be used in the compositions of this invention, most preferably the one or more glyphosate salts constitute(s) the only herbicide(s) or plant growth regulant(s) used in forming the compositions of this invention. Likewise, most preferably the herein-described combinations of components (b) and (c) constitute the only surfactants used in the practice of this invention. The use of component (a) as the sole herbicide(s) or plant growth regulant(s), and components (b) and (c) as the only surfactants ensures that the substantial benefits provided by this invention are realized in full.

The powder or granular formulations of this invention may be mixed with a finely-divided solid diluent such as talc, gypsum, Fuller's earth, kaolin, kieselguhr, bentonite, dolomite, calcium carbonate, and powdered magnesia. They may also be formulated as dispersible powders or grains, and in this case it is desirable to include a wetting agent to facilitate the dispersion of powder or grains in the liquid carrier. Additionally, formulations in the form of powders can be applied to vegetation as foliar dusts.

It is to be understood that the terms "ingredient" or "component" or "substance" as used anywhere in the specification or claims hereof, whether used in the singular or plural, are used in the sense that it is a substance employed in forming the powder or granular concentrate or aqueous solution, and thus at least prior to mixing with other ingredients or components and/or addition to an aqueous medium, the ingredient or component is in the chemical form specified. It matters not what chemical changes, transformations and/or reactions, if any, take place in the mixture or aqueous medium itself as such changes, transformations and/or reactions are the natural result of bringing the specified ingredients or components together as solids or in an aqueous medium.

Each and every patent or other publication referred to in any portion of this specification is fully incorporated into this disclosure by reference as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A method of controlling vegetation which comprises applying to plant foliage a herbicidal or growth regulant amount of a composition formed by intimately mixing the following components with water:

a) at least one agriculturally acceptable salt of glyphosate;

b) at least one water-soluble long chain aliphatic hydrocarbyl dimethyl amine oxide in which the hydrocarbyl group is a linear or substantially linear saturated or olefinically unsaturated aliphatic group having in the range of about 8 to about 22 carbon atoms; and c) at least one water-soluble quaternary ammonium halide having in the range of about 8 to about 40 carbon atoms in the molecule, and depicted by the formula:

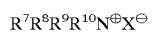

$$R^7R^8R^9R^{10}N^{\oplus}X^{\ominus}$$

where $R^7$ is a saturated or olefinically unsaturated aliphatic hydrocarbyl group having in the range of about 6 to about 24 carbon atoms, $R^8$ is an alkyl group having 1 to 4 carbon atoms, $R^9$ is a hydroxyalkyl group having from 2 to about 4 carbon atoms, $R^{10}$ is, independently, either an alkyl group having 1 to 4 carbon atoms or a hydroxyalkyl group having from 2 to about 4 carbon atoms, and X is a halogen atom.

2. A method according to claim 1 wherein component a) is an amine or alkylsulfonium salt of glyphosate.

3. A method according to claim 1 wherein component a) is the isopropyl amine salt of glyphosate.

4. A method according to claim 1 wherein component a) is the only herbicide used in forming said composition.

5. A method according to claim 1 wherein said water-soluble quaternary ammonium halide is a chloride or bromide.

6. A method according to claim 1 wherein said water-soluble amine oxide is one or more alkyl dimethyl amine oxides in which the alkyl group contains about 8 to about 16 carbon atoms, and wherein said water-soluble quaternary ammonium halide is one or more quaternary ammonium halides in which $R^7$ has in the range of about 10 to about 18 carbon atoms, $R^8$ is an alkyl group having 1 or 2 carbon atoms, $R^9$ is a hydroxyalkyl group having from 2 to about 4 carbon atoms, $R^{10}$ is, independently, an alkyl group having 1 or 2 carbon atoms or a hydroxyalkyl group having from 2 to about 4 carbon atoms, and X is a bromine or chlorine atom, and where the total number of carbon atoms in $R^7$, $R^8$, $R^9$, and $R^{10}$ is up to about 30 carbon atoms.

7. A method according to claim 1 wherein component a) is an amine or alkylsulfonium salt of glyphosate, wherein said water-soluble amine oxide is one or more alkyl dimethyl amine oxides in which the alkyl group contains about 8 to about 16 carbon atoms, and and wherein said water-soluble quaternary ammonium halide is one or more quaternary ammonium halides in which $R^7$ has in the range of about 10 to about 18 carbon atoms, $R^8$ is an alkyl group having 1 or 2 carbon atoms, $R^9$ is a 2-hydroxyethyl group, $R^{10}$ is, independently, an alkyl group having 1 or 2 carbon atoms or a 2-hydroxyethyl group, and X is a bromine or chlorine atom, and where the total number of carbon atoms in $R^7$, $R^8$, $R^9$, and $R^{10}$ is up to about 22 carbon atoms.

8. A method according to claim 7 wherein said water-soluble quaternary ammonium halide is one or more quaternary ammonium halides in which $R^7$ has in the range of about 10 to about 18 carbon atoms, $R^8$ is a methyl group, $R^9$ is a 2-hydroxyethyl group, $R^{10}$ is, independently, a methyl group or a 2-hydroxyethyl group.

9. A method according to claim 8 wherein component a) is the isopropyl amine salt of glyphosate and wherein said water-soluble quaternary ammonium halide is one or more quaternary ammonium bromides.

10. A method according to claim 8 wherein component a) is an amine salt of glyphosate and wherein said water-soluble quaternary ammonium halide is (i) one or more $C_{10-14}$ monoalkyl methyl diethanol quaternary ammonium chlorides, (ii) one or more $C_{10-14}$ monoalkyl methyl diethanol quaternary ammonium bromides, (iii) one or more $C_{10-14}$ monoalkyl dimethyl ethanol quaternary ammonium chlorides, (iv) one or more $C_{10-14}$ monoalkyl dimethyl ethanol quaternary ammonium bromides or (v) any combination of at least two of (i), (ii), (iii), and (iv).

11. A method according to claim 8 wherein component a) is the isopropyl amine salt of glyphosate and wherein said water-soluble quaternary ammonium halide is (i) one or more $C_{10-14}$ monoalkyl methyl diethanol quaternary ammonium chlorides wherein the $C_{10-14}$ alkyl group is a linear primary alkyl group, (ii) one or more $C_{10-14}$ monoalkyl methyl diethanol quaternary ammonium bromides wherein the $C_{10-14}$ alkyl group is a linear primary alkyl group, (iii) one or more $C_{10-14}$ monoalkyl dimethyl ethanol quaternary ammonium chlorides wherein the $C_{10-14}$ alkyl group is a linear primary alkyl group, (iv) one or more $C_{10-14}$ monoalkyl dimethyl ethanol quaternary ammonium bromides wherein the $C_{10-14}$ alkyl group is a linear primary alkyl group, or (v) any combination of at least two of (i), (ii), (iii), and (iv).

12. A composition which comprises a solution containing at least a herbicidally or plant growth regulating amount of a composition formed by intimately mixing the following components with water:

a) at least one agriculturally acceptable salt of glyphosate;

b) at least one water-soluble long chain aliphatic hydrocarbyl dimethyl amine oxide in which the hydrocarbyl group is a linear or substantially linear saturated or olefinically unsaturated aliphatic group having in the range of about 8 to about 22 carbon atoms; and c) at least one water-soluble quaternary ammonium halide having in the range of about 8 to about 40 carbon atoms in the molecule, and depicted by the formula:

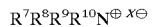

where $R^7$ is a saturated or olefinically unsaturated aliphatic hydrocarbyl group having in the range of about 6 to about 24 carbon atoms, $R^8$ is an alkyl group having 1 to 4 carbon atoms, $R^9$ is a hydroxyalkyl group having from 2 to about 4 carbon atoms, $R^{10}$ is, independently, either an alkyl group having 1 to 4 carbon atoms or a hydroxyalkyl group having from 2 to about 4 carbon atoms, and X is a halogen atom.

13. A composition according to claim 12 wherein component a) is an amine, ammonium, alkali metal, alkylsulfonium, alkylphosphonium, sulfonylamine, and/or aminoguanidine salt of glyphosate.

14. A composition according to claim 12 wherein component a) is an amine or alkylsulfonium salt of glyphosate.

15. A composition according to claim 12 wherein component a) is the isopropyl amine salt of glyphosate.

16. A composition according to claim 12 wherein component a) thereof is the only herbicide used in forming said composition.

17. A composition according to claim 12 wherein said water-soluble quaternary ammonium halide is a chloride or bromide.

18. A composition according to claim 12 wherein said water-soluble amine oxide is one or more alkyl dimethyl amine oxides in which the alkyl group contains about 8 to about 16 carbon atoms, and wherein said water-soluble quaternary ammonium halide is one or more quaternary ammonium halides in which $R^7$ has in the range of about 10 to about 18 carbon atoms, $R^8$ is an alkyl group having 1 or 2 carbon atoms, $R^9$ is a hydroxyalkyl group having from 2 to about 4 carbon atoms, $R^{10}$ is, independently, an alkyl group having 1 or 2 carbon atoms or a hydroxyalkyl group having from 2 to about 4 carbon atoms, and X is a bromine or chlorine atom, and where the total number of carbon atoms in $R^7$, $R^8$, $R^9$, and $R^{10}$ is up to about 30 carbon atoms.

19. A composition according to claim 12 wherein component a) is an amine or alkylsulfonium salt of glyphosate, wherein said water-soluble amine oxide is one or more alkyl dimethyl amine oxides in which the alkyl group contains about 8 to about 16 carbon atoms, and and wherein said water-soluble quaternary ammonium halide is one or more quaternary ammonium halides in which $R^7$ has in the range of about 10 to about 18 carbon atoms, $R^8$ is an alkyl group having 1 or 2 carbon atoms, $R^9$ is a 2-hydroxyethyl group, $R^{10}$ is, independently, an alkyl group having 1 or 2 carbon atoms or a 2-hydroxyethyl group, and X is a bromine or chlorine atom, and where the total number of carbon atoms in $R^7$, $R^8$, $R^9$, and $R^{10}$ is up to about 22 carbon atoms.

20. A composition according to claim 19 wherein said water-soluble quaternary ammonium halide is one or more quaternary ammonium halides in which $R^7$ has in the range of about 10 to about 18 carbon atoms, $R^8$ is a methyl group, $R^9$ is a 2-hydroxyethyl group, $R^{10}$ is, independently, a methyl group or a 2-hydroxyethyl group.

21. A composition according to claim 20 wherein component a) is the isopropyl amine salt of glyphosate and wherein said water-soluble quaternary ammonium halide is one or more quaternary ammonium bromides.

22. A composition according to claim 20 wherein component a) is an amine salt of glyphosate and wherein said water-soluble quaternary ammonium halide is (i) one or more $C_{10-14}$ monoalkyl methyl diethanol quaternary ammonium chlorides, (ii) one or more $C_{10-14}$ monoalkyl methyl diethanol quaternary ammonium bromides, (iii) one or more $C_{10-14}$ monoalkyl dimethyl ethanol quaternary ammonium chlorides, (iv) one or more $C_{10-14}$ monoalkyl dimethyl ethanol quaternary ammonium bromides or (v) any combination of at least two of (i), (ii), (iii), and (iv).

23. A composition according to claim 20 wherein component a) is the isopropyl amine salt of glyphosate and wherein said water-soluble quaternary ammonium halide is (i) one or more $C_{10-14}$ monoalkyl methyl diethanol quaternary ammonium chlorides wherein the $C_{10-14}$ alkyl group is a linear primary alkyl group, (ii) one or more $C_{10-14}$ monoalkyl methyl diethanol quaternary ammonium bromides wherein the $C_{10-14}$ alkyl group is a linear primary alkyl group, (iii) one or more $C_{10-14}$ monoalkyl dimethyl ethanol quaternary ammonium chlorides wherein the $C_{10-14}$ alkyl group is a linear primary alkyl group, (iv) one or more $C_{10-14}$ monoalkyl dimethyl ethanol quaternary ammonium bromides wherein the $C_{10-14}$ alkyl group is a linear primary alkyl group, or (v) any combination of at least two of (i), (ii), (iii), and (iv).

24. A composition according to claim 12 wherein the solution is devoid of metal and metalloid additive content other than the phosphorus of the glyphosate, and is formed using deionized water.

25. A composition according to claim 24 wherein component a) is an amine salt of glyphosate, wherein the weight ratio of components b) and c) used in forming said solution is in the range of about 3:1 to about 1:3, respectively, and wherein said solution is an aqueous concentrate adapted for dilution with water before use.

26. A composition according to claim 24 wherein component a) is an amine salt of glyphosate, wherein the weight ratio of components b) and c) used in forming said solution is in the range of about 3:1 to about 1:3, respectively, and wherein said solution is a dilute water solution adapted for direct application to at least one plant species.

27. A composition which comprises a powder or granular mixture containing at least a herbicidally or plant growth regulating amount of a composition formed by intimately mixing together the following components:
   a) at least one agriculturally acceptable salt of glyphosate;
   b) at least one water-soluble long chain aliphatic hydrocarbyl dimethyl amine oxide in which the hydrocarbyl group is a linear or substantially linear saturated or olefinically unsaturated aliphatic group having in the range of about 8 to about 22 carbon atoms; and
   c) at least one water-soluble quaternary ammonium halide having in the range of about 8 to about 40 carbon atoms in the molecule, and depicted by the formula:

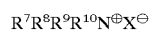

where $R^7$ is a saturated or olefinically unsaturated aliphatic hydrocarbyl group having in the range of about 6 to about 24 carbon atoms, $R^8$ is an alkyl group having 1 to 4 carbon atoms, $R^9$ is a hydroxyalkyl group having from 2 to about 4 carbon atoms, $R^{10}$ is, independently, either an alkyl group having 1 to 4 carbon atoms or a hydroxyalkyl group having from 2 to about 4 carbon atoms, and X is a halogen atom.

28. A composition according to claim 27 wherein component a) is an amine, ammonium, alkali metal, alkylsulfonium, alkylphosphonium, sulfonylamine, and/or aminoguanidine salt of glyphosate.

29. A composition according to claim 27 wherein component a) is an amine or alkylsulfonium salt of glyphosate.

30. A composition according to claim 27 wherein said water-soluble amine oxide is one or more alkyl dimethyl amine oxides in which the alkyl group contains about 8 to about 16 carbon atoms, and wherein said water-soluble quaternary ammonium halide is one or more quaternary ammonium halides in which $R^7$ has in the range of about 10 to about 18 carbon atoms, $R^8$ is an alkyl group having 1 or 2 carbon atoms, $R^9$ is a hydroxyalkyl group having from 2 to about 4 carbon atoms, $R^{10}$ is, independently, an alkyl group having 1 or 2 carbon atoms or a hydroxyalkyl group having from 2 to about 4 carbon atoms, and X is a bromine or chlorine atom, and where the total number of carbon atoms in $R^7$, $R^8$, $R^9$, and $R^{10}$ is up to about 30 carbon atoms.

31. A composition according to claim 27 wherein component a) is an amine or alkylsulfonium salt of glyphosate, wherein said water-soluble amine oxide is one or more alkyl dimethyl amine oxides in which the alkyl group contains about 8 to about 16 carbon atoms, and and wherein said water-soluble quaternary ammonium halide is one or more quaternary ammonium halides in which $R^7$ has in the range of about 10 to about 18 carbon atoms, $R^8$ is an alkyl group having 1 or 2 carbon atoms, $R^9$ is a 2-hydroxyethyl group, $R^{10}$ is, independently, an alkyl group having 1 or 2 carbon atoms or a 2-hydroxyethyl group, and X is a bromine or chlorine atom, and where the total number of carbon atoms in $R^7$, $R^8$, $R^9$, and $R^{10}$ is up to about 22 carbon atoms.

32. A composition according to claim 27 wherein said water-soluble quaternary ammonium halide is one or more quaternary ammonium halides in which $R^7$ has in the range of about 10 to about 18 carbon atoms, $R^8$ is a methyl group, $R^9$ is a 2-hydroxyethyl group, $R^{10}$ is, independently, a methyl group or a 2-hydroxyethyl group.

33. A composition according to claim 27 wherein component a) is the isopropyl amine salt of glyphosate and wherein said water-soluble quaternary ammonium halide is one or more quaternary ammonium bromides.

34. A composition according to claim 27 wherein component a) is an amine salt of glyphosate and wherein said water-soluble quaternary ammonium halide is (i) one or more $C_{10-14}$ monoalkyl methyl diethanol quaternary ammonium chlorides, (ii) one or more $C_{10-14}$ monoalkyl methyl diethanol quaternary ammonium bromides, (iii) one or more $C_{10-14}$ monoalkyl dimethyl ethanol quaternary ammonium chlorides, (iv) one or more $C_{10-14}$ monoalkyl dimethyl ethanol quaternary ammonium bromides or (v) any combination of at least two of (i), (ii), (iii), and (iv).

35. A composition according to claim 34 wherein component a) is the isopropyl amine salt of glyphosate and wherein said water-soluble quaternary ammonium halide is (i) one or more $C_{10-14}$ monoalkyl methyl diethanol quaternary ammonium chlorides wherein the $C_{10-14}$ alkyl group is a linear primary alkyl group, (ii) one or more C$_{10-14}$ monoalkyl methyl diethanol quaternary ammonium bromides wherein the C$_{10-14}$ alkyl group is a linear primary alkyl group, (iii) one or more C$_{10-14}$ monoalkyl dimethyl ethanol quaternary ammonium chlorides wherein the C$_{10-14}$ alkyl group is a linear primary alkyl group, (iv) one or more C$_{10-14}$ monoalkyl dimethyl ethanol quaternary ammonium bromides wherein the C$_{10-14}$ alkyl group is a linear primary alkyl group, or (v) any combination of at least two of (i), (ii), (iii), and (iv).

36. A composition according to claim 31 wherein said composition consists of said components a), b) and c).

37. A method of controlling vegetation which comprises applying to plant foliage a herbicidal or plant growth regulant amount of a polyvalent metal-free and metalloid-free herbicide or plant growth regulant composition formed by intimately mixing together the following ingredients:
   a) at least one agriculturally acceptable salt of glyphosate as the only herbicide or plant growth regulant used in forming said composition;
   b) at least one water-soluble long chain aliphatic hydrocarbyl dimethyl amine oxide in which the hydrocarbyl group is a linear or substantially linear saturated or olefinically unsaturated aliphatic group having in the range of about 8 to about 22 carbon atoms;
   c) at least one water-soluble quaternary ammonium halide having in the range of about 8 to about 40 carbon atoms in the molecule, and depicted by the formula:

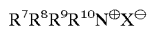

$$R^7R^8R^9R^{10}N^{\oplus}X^{\ominus}$$

where R$^7$ is a saturated or olefinically unsaturated aliphatic hydrocarbyl group having in the range of about 6 to about 24 carbon atoms, R$^8$ is an alkyl group having 1 to 4 carbon atoms, R$^9$ is a hydroxyalkyl group having from 2 to about 4 carbon atoms, R$^{10}$ is, independently, either an alkyl group having 1 to 4 carbon atoms or a hydroxyalkyl group having from 2 to about 4 carbon atoms, and X is a halogen atom, ingredients b) and c) being the only surfactants used in forming said composition; and
   d) optionally, one or more agriculturally acceptable substances none of which is a herbicide, or a plant growth regulant or a surfactant.

38. A method according to claim 37 wherein said herbicide or plant growth regulant composition is a water solution, and wherein said composition is applied to the foliage by spraying the water solution onto the foliage.

39. A method according to claim 37 wherein said herbicide or plant growth regulant composition is in the form of a powder, and wherein said composition is applied to the foliage as a foliar dust.

40. A method according to claim 37 wherein component a) is an amine, ammonium, alkali metal, alkylsulfonium, alkylphosphonium, sulfonylamine, and/or aminoguanidine salt of glyphosate.

41. A method according to claim 1 wherein said composition is applied at a rate such that the rate of application of the glyphosate, on an acid equivalent basis, is in the range of about 200 to about 830 grams per hectare.

42. A method according to claim 37 wherein said composition is applied at a rate such that the rate of application of the glyphosate, on an acid equivalent basis, is in the range of about 200 to about 830 grams per hectare.

43. A method according to claim 1 wherein said components consist of a), b), and c).

44. A method according to claim 43 wherein component a) is an amine or alkylsulfonium salt of glyphosate; wherein component b) is at least one alkyl dimethyl amine oxide in which said alkyl group contains about 8 to about 16 carbon atoms; wherein in component c) R$^7$ has in the range of about 10 to about 18 carbon atoms, R$^8$ is an alkyl group having 1 or 2 carbon atoms, R$^9$ is a hydroxyalkyl group having from 2 to about 4 carbon atoms, R$^{10}$, is, independently, an alkyl group having 1 or 2 carbon atoms or a hydroxyalkyl group having from 2 to about 4 carbon atoms, and X is a bromine or chlorine atom; wherein the total number of carbon atoms in R$^7$, R$^8$, R$^9$, and R$^{10}$ is up to about 30 carbon atoms; and wherein said composition is applied at a rate such that the rate of application of the glyphosate, on an acid equivalent basis, is in the range of about 200 to about 830 grams per hectare.

45. A composition according to claim 12 wherein said components consist of a), b), and c).

46. A composition according to claim 45 wherein component a) is an amine or alkylsulfonium salt of glyphosate; wherein component b) is at least one alkyl dimethyl amine oxide in which said alkyl group contains about 8 to about 16 carbon atoms; wherein in component c) R$^7$ has in the range of about 10 to about 18 carbon atoms, R$^8$ is an alkyl group having 1 or 2 carbon atoms, R$^9$ is a hydroxyalkyl group having from 2 to about 4 carbon atoms, R$^{10}$, is, independently, an alkyl group having 1 or 2 carbon atoms or a hydroxyalkyl group having from 2 to about 4 carbon atoms, and X is a bromine or chlorine atom; and wherein the total number of carbon atoms in R$^7$, R$^8$, R$^9$, and R$^{10}$ is up to about 30 carbon atoms.

47. A composition according to claim 27 wherein said components consist of a), b), and c).

48. A composition according to claim 47 wherein component a) is an amine or alkylsulfonium salt of glyphosate; wherein component b) is at least one alkyl dimethyl amine oxide in which said alkyl group contains about 8 to about 16 carbon atoms; wherein in component c) R$^7$ has in the range of about 10 to about 18 carbon atoms, R$^8$ is an alkyl group having 1 or 2 carbon atoms, R$^9$ is a hydroxyalkyl group having from 2 to about 4 carbon atoms, R$^{10}$, is, independently, an alkyl group having 1 or 2 carbon atoms or a hydroxyalkyl group having from 2 to about 4 carbon atoms, and X is a bromine or chlorine atom; and wherein the total number of carbon atoms in R$^7$, R$^8$, R$^9$, and R$^{10}$ is up to about 30 carbon atoms.

49. A method according to claim 37 wherein said ingredients consist of a), b), and c).

50. A method according to claim 49 wherein component a) is an amine or alkylsulfonium salt of glyphosate; wherein component b) is at least one alkyl dimethyl amine oxide in which said alkyl group contains about 8 to about 16 carbon atoms; wherein in component c) R$^7$ has in the range of about 10 to about 18 carbon atoms, R$^8$ is an alkyl group having 1 or 2 carbon atoms, R$^9$ is a hydroxyalkyl group having from 2 to about 4 carbon atoms, R$^{10}$, is, independently, an alkyl group having 1 or 2 carbon atoms or a hydroxyalkyl group having from 2 to about 4 carbon atoms, and X is a bromine or chlorine atom; wherein the total number of carbon atoms in R$^7$, R$^8$, R$^9$, and R$^{10}$ is up to about 30 carbon atoms; and wherein said composition is applied at a rate such that the rate of application of the glyphosate, on an acid equivalent basis, is in the range of about 200 to about 830 grams per hectare.

* * * * *